US008778894B2

(12) United States Patent
Tan et al.

(10) Patent No.: US 8,778,894 B2
(45) Date of Patent: Jul. 15, 2014

(54) LUTEOLIN AND DIOSMIN/DIOSMETIN AS NOVEL STAT3 INHIBITORS FOR TREATING AUTISM

(71) Applicants: Jun Tan, Tampa, FL (US); Deyan Luo, Saranac Lake, NY (US); Roland Douglas Shytle, Largo, FL (US)

(72) Inventors: Jun Tan, Tampa, FL (US); Deyan Luo, Saranac Lake, NY (US); Roland Douglas Shytle, Largo, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/046,381

(22) Filed: Oct. 4, 2013

(65) Prior Publication Data

US 2014/0038913 A1     Feb. 6, 2014

Related U.S. Application Data

(63) Continuation of application No. 13/093,401, filed on Apr. 25, 2011, now abandoned, which is a continuation of application No. PCT/US2009/062753, filed on Oct. 30, 2009.

(60) Provisional application No. 61/109,538, filed on Oct. 30, 2008.

(51) Int. Cl.
*A01N 43/04* (2006.01)
*A61K 31/70* (2006.01)
*A01N 43/16* (2006.01)
*A61K 31/35* (2006.01)

(52) U.S. Cl.
USPC ............................................. 514/27; 514/457

(58) Field of Classification Search
None
See application file for complete search history.

(56) References Cited

U.S. PATENT DOCUMENTS

| | | | |
|---|---|---|---|
| 2003/0194719 A1 | 10/2003 | Waring et al. | |
| 2004/0152640 A1* | 8/2004 | Van Helvoort et al. | 514/27 |
| 2004/0234587 A1 | 11/2004 | Sampalis | |
| 2005/0276872 A1 | 12/2005 | Chan et al. | |
| 2006/0182747 A1 | 8/2006 | Skurkovich et al. | |
| 2008/0015247 A1 | 1/2008 | Lines | |
| 2008/0176934 A1* | 7/2008 | Verbeuren et al. | 514/456 |

OTHER PUBLICATIONS

Parker-Athill et al. (Journal of Neuroimmunology 217 (2009) 20-27, published online Sep. 18, 2008.*
Ashdown et al. (Molecular Psychiatry (2006) 11, 47-55.*
Honda, Flavonoids Benefit Oxidative Stress and Inflammation Associated with Autism, ARCH Neurol., 2006, vol. 63, pp. 1161-1164.
Agarwal et al., Silibinin Inhibits Constitutive Activation of Stat3, and Causes Caspase Activation and Apoptotic Death of Human Prostate Carcinoma DU145 Cells, Carcinogenesis, 2007, vol. 28, No. 7, pp. 1463-1470.
Vargas et al., Neuroglial Activation and Neuroinflammation in the Brain of Patients with Autism, Ann. Neurol., 2005, vol. 57, pp. 67-81.
Behrens et al., Interleukin-6 Mediates the Increase in NADPH-Oxidase in the Ketamine Model of Schizophrenia, The Journal of Neuroscience, 2008, vol. 28, No. 51, pp. 13957-13966.
Smith et al., Maternal Immune Activation Alters Fetal Brain Development Through Interleukin-6, The Journal of Neuroscience, 2007, vol. 27, No. 40, pp. 10695-10702.
Parker-Athill et al., Flavonoids, a Prenatal Prophylaxis Via Targeting JAK2/STAT3 Signaling to Oppose IL-6/MIA Associated Autism, Journal of Neuroimmunology, 2009, vol. 217, pp. 20-27.
Fatemi et al., The Neurodevelopmental Hypothesis of Schizophrenia, Revisited, Schizophrenia Bulletin, 2009, vol. 35, No. 3, pp. 528-548.
Glund et al., Interleukin-6 Directly Increases Glucose Metabolism in Resting Human Skeletal Muscle, Diabetes, 2007, vol. 56, pp. 1630-1637.
Braff et al., Human Studies of Prepulse Inhibition of Startle: Normal Subjects, Patient Groups, and Pharmacological Studies, Psychopharmacology, 2001, vol. 156, pp. 234-258.
He et al., A Positive Autoregulatory Loop of Jak-STAT Signaling Controls the Onset of Astrogliogenesis, Nature Neuroscience, 2005, vol. 8, No. 5, pp. 616-625.
Fatemi et al., Prenatal Viral Infection in Mouse Causes Differential Expression of Genes in Brains of Mouse Progeny: A Potential Animal Model for Schizophrenia and Autism, Synapse, 2005, vol. 57, pp. 91-99.
Fatemi et al., Maternal Infection Leads to Abnormal Gene Regulation and Brain Atrophy in Mouse Offspring: Implications for Genesis of Neurodevelopmental Disorders, Schizophrenia Research, 2008, vol. 99, pp. 56-70.
Frankland et al., Sensorimotor Gating Abnormalities in Young Males With Fragile X Syndrome and Fmr1-Knockout Mice, Molecular Psychiatry, 2004, vol. 9, pp. 417-425.
Kim et al., Luteolin Inhibits the Nuclear Factor-KappaB Transcriptional Activity in Rat-1 Fibroblasts, Biochemical Pharmacology, 2003, vol. 66, pp. 955-963.
Kim et al., The Flavonoid Luteolin Prevents LPS-Induced NF-KappaB Signaling and Gene Expression by Blocking IKappaB Kinase Activity in Intestinal Epithelial Cells and Bone Marrow-Derived Dendritic Cells, Immunology, 2005, vol. 115, pp. 375-387.

(Continued)

*Primary Examiner* — Layla Bland
(74) *Attorney, Agent, or Firm* — Michele L. Lawson; Smith & Hopen, P. A.

(57) ABSTRACT

The present invention includes methods for the treatment of autoimmune disorders such as autism, schizophrenia, and type 1 diabetes. Flavonoids, luteolin, diosmin, and diosmin's aglycone form, diosmetin, were found to inhibit activation/phosphorylation of STAT3 induced by IL-6 in cultured neuronal cells. Furthermore, mice treated with diosmin showed a significant reduction of autistic phenotype induced by IL-6 through inhibition of STAT3 activation.

15 Claims, 3 Drawing Sheets

(56) References Cited

OTHER PUBLICATIONS

Shimoi et al., Intestinal Absorption of Luteolin and Luteolin 7-O-Beta-Glucoside in Rats and Humans, FEBS Letters, 1998, vol. 438, pp. 220-224.

Simpson et al., Insulin-Like Growth Factor I Has a Direct Effect on Glucose and Protein Metabolism, But no Effect on Lipid Metabolism in Type 1 Diabetes, The Journal of Clinical Endocrinology & Metabolism, 2004, vol. 89, No. 1, pp. 425-432.

Xagorari et al., Luteolin Inhibits an Endotoxin-Stimulated Phosphorylation Cascade and Proinflammatory Cytokine Production in Macrophages, The Journal of Pharmacology and Experimental Therapeutics, 2001, vol. 296, No. 1, pp. 181-187.

Kang et al., Interleukin-6 Induces Proliferation in Adult Spinal Cord-Derived Neural Progenitors Via the JAK2/STAT3 Pathway with EGF-Induced MAPK Phosphorylation, Cell Proliferation, 2008, vol. 41, pp. 377-392.

Mostofsky et al., Increased Motor Cortex White Matter Volume Predicts Motor Impairment in Autism, Brain, 2007, vol. 130, pp. 2117-2122.

Labrid, Pharmacologic Properties of Daflon 500 mg, Angiology, The Journal of Vascular Diseases, 1994, vol. 45, No. 6, Part 2, pp. 524-530.

Mlakar et al., Flavonoids to Reduce Bleeding and Pain After Stapled Hemorrhoidopexy: a Randomized Controlled Trial, Wiener Klinische Wochenschrift, The Middle European Journal of Medicine, 2005, vol. 117, No. 15-16, pp. 558-560.

Lyseng-Williamson et al., Micronised Purified Flavonoid Fraction, A Review of Its Use in Chronic Venous Insufficiency, Venous Ulcers and Haemorrhoids, Drugs, 2003, vol. 63, No. 1, pp. 71-100.

Meyer et al., The Time of Prenatal Immune Challenge Determines the Specificity of Inflammation-Mediated Brain and Behavioral Pathology, The Journal of Neuroscience, 2006, vol. 26, No. 18, pp. 4752-4762.

Paintlia et al., N-Acetylcysteine Prevents Endotoxin-Induced Degeneration of Oligodendrocyte Progenitors and Hypomyelination in Developing Rat Brain, Journal of Neuroscience Research, 2004, vol. 78, pp. 347-361.

Shi et al., Maternal Influenza Infection is Likely to Alter Fetal Brain Development Indirectly: The Virus is not Detected in the Fetus, International Journal of Developmental Neuroscience, 2005, vol. 23, pp. 299-305.

Pizzi et al., Prevention of Neuron and Oligodendrocyte Degeneration by Interleukin-6 (IL-6) and IL-6 Receptor/IL-6 Fusion Protein in Organotypic Hippocampal Slices, Molecular and Cellular Neuroscience, 2004, vol. 25, pp. 301-311.

Schindler et al., Transcriptional Responses to Polypeptide Ligands: The JAK-STAT Pathway, Annu. Rev. Biochem., 1995, vol. 64, pp. 621-651.

Van Wagoner et al., Interleukin-6 Expression and Regulation in Astrocytes, Journal of Neuroimmunology, 1999, vol. 100, pp. 124-139.

Shi et al., Maternal Influenza Infection Causes Marked Behavioral and Pharmacological Changes in the Offspring, The Journal of Neuroscience, 2003, vol. 23, No. 1, pp. 297-302.

Xu et al., Tumor Necrosis Factor Alpha Partially Contributes to Lipopolysaccharide-Induced Intra-Uterine Fetal Growth Restriction and Skeletal Development Retardation in Mice, Toxicology Letters, 2006, vol. 163, pp. 20-29.

Urakubo et al., Prenatal Exposure to Maternal Infection Alters Cytokine Expression in the Placenta, Amniotic Fluid, and Fetal Brain, Schizophrenia Research, 2001, vol. 47, pp. 27-36.

Gadient et al., Identification of Interleukin-6 (IL-6)-Expressing Neurons in the Cerebellum and Hippocampus of Normal Adult Rats, Neuroscience Letters, 1994, vol. 182, pp. 243-246.

Giunta et al., Neuroprotection of Green Tea Derived EGCG: Implications for HIV Associated Dementia, The FASEB Journal, 2007, vol. 21, No. 6, pp. A1175-A1175.

Gayle et al., Maternal LPS Induces Cytokines in the Amniotic Fluid and Corticotropin Releasing Hormone in the Fetal Rat Brain, Am. J. Physiol. Regul. Integr. Comp. Physiol., 2004, vol. 286, pp. R1024-R1029.

Gilmore et al., Maternal Poly I:C Exposure During Pregnancy Regulates TNFAlpha, BDNF, and NGF Expression in Neonatal Brain and the Maternal-Fetal Unit of the Rat, Journal of Neuroimmunology, 2005, vol. 159, pp. 106-112.

Giunta et al., EGCG Mitigates Neurotoxicity Mediated by HIV-1 Proteins gp120 and TAT in the Presence of IFN-Gamma: Role of JAK/STAT1 Signaling and Implications for HIV-Associated Dementia, Brain Research, 2006, vol. 1123, pp. 216-225.

Gadient et al., Interleukin-6 (IL-6)-A Molecule with Both Beneficial and Destructive Potentials, Progress in Neurobiology, 1997, vol. 52, pp. 379-390.

John et al., Cytokines: Powerful Regulators of Glial Cell Activation, The Neuroscientist, 2003, vol. 9, pp. 10-22.

Kamimura et al., IL-6 Signal Transduction and Its Physiological Roles: The Signal Orchestration Model, Rev. Physiol. Biochem. Pharmacol., 2003, vol. 149, pp. 1-38.

Fidel et al., Systemic and Local Cytokine Profiles in Endotoxin-Induced Preterm Parturition in Mice, Am. J. Obstet. Gynecol., 1994, vol. 170, pp. 1467-1475.

Akira et al., Biology of Multifunctional Cytokines: IL 6 and Related Molecules (IL 1 and TNF), FASEB Journal, 1990, vol. 4, pp. 2860-2867.

Arndt et al., The Teratology of Autism, International Journal of Developmental Neuroscience, 2005, vol. 23, pp. 189-199.

Ashdown et al., The Role of Cytokines in Mediating Effects of Prenatal Infection on the Fetus: Implications for Schizophrenia, Molecular Psychiatry, 2006, vol. 11, pp. 47-55.

Aylward et al., Effects of Age on Brain Volume and Head Circumference in Autism, Neurology, 2002, vol. 59, pp. 175-183.

Bashat et al., Accelerated Maturation of White Matter in Young Children with Autism: A High b Value DWI Study, NeuroImage, 2007, vol. 37, pp. 40-47.

Bauer et al., The Neuropoietic Cytokine Family in Development, Plasticity, Disease and Injury, Nature Reviews Neuroscience, 2007, vol. 8, pp. 221-232.

Beloosesky et al., N-Acetyl-Cysteine Suppresses Amniotic Fluid and Placenta Inflammatory Cytokine Responses to Lipopolysaccharide in Rats, American Journal of Obstetrics & Gynecology, 2006, vol. 194, pp. 268-273.

Cai et al., Cytokine Induction in Fetal Rat Brains and Brain Injury in Neonatal Rats After Maternal Lipopolysaccharide Administration, Pediatric Research, 2000, vol. 47, No. 1, pp. 64-72.

Courchesne et al., Evidence of Brain Overgrowth in the First Year of Life in Autism, JAMA, 2003, vol. 290, No. 3, pp. 337-344.

Cova et al., Pharmacokinetics and Metabolism of Oral Diosmin in Healthy Volunteers, International Journal of Clinical Pharmacology, Therapy and Toxicology, 1992, vol. 30, No. 1, pp. 29-33.

Giunta et al., HIV-1 TAT Inhibits Microglial Phagocytosis of ABeta Peptide, Int. J. Clin. Exp. Path., 2008, vol. 1, pp. 260-275.

Hamma et al., Syntheses of Alternating Oligo-2'-O-Methylribonucleoside Methylphosphonates and Their Interactions with HIV TAR RNA, Biochemistry, 1999, vol. 38, pp. 15333-15342.

Huleihel et al., Intrauterine Infection/Inflammation During Pregnancy and Offspring Brian Damages: Possible Mechanisms Involved, Reproductive Biology and Endocrinology, 2004, vol. 2, pp. 17-24.

Ebong et al., Characterization of the Roles of STAT1 and STAT3 Signal Transduction Pathways in Mammalian Lens Development, Molecular Vision, 2004, vol. 10, pp. 122-131.

Courchesne et al., Unusual Brian Growth Patterns in Early Life in Patients with Autistic Disorder, An MRI Study, Neurology, 2001, vol. 57, pp. 245-254.

Heinrich et al., Interleukin-6-Type Cytokine Signaling Through the gp130/Jak/STAT Pathway, Biochem. J., 1998, vol. 334, pp. 297-314.

Falutz et al., Metabolic Effects of a Growth Hormone-Releasing Factor in Patients with HIV, The New England Journal of Medicine, 2007, vol. 357, pp. 2359-2370.

(56) References Cited

OTHER PUBLICATIONS

Kuntz et al., Comparative Analysis of the Effects of Flavonoids on Proliferation, Cytotoxicity, and Apoptosis in Human Colon Cancer Cell Lines, Eur. J. Nutr., 1999, vol. 38, pp. 133-142.
Comalada et al., Inhibition of Pro-Inflammatory Markers in Primary Bone Marrow-Derived Mouse Macrophages by Naturally Occurring Flavonoids: Analysis of the Structure-Activity Relationship, Biochemical Pharmacology, 2006, vol. 72, pp. 1010-1021.
Jagtap et al., Chemoprotective Mechanism of the Natural Compounds, Epigallocate-Chin-3-O-Gallate, Quercetin and Curcumin Against Cancer and Cardiovascular Diseases, Current Medicinal Chemistry, 2009, vol. 16, pp. 1451-1462.
Jantet, Relief Study: First Consolidated European Data, Angiology, The Journal of Vascular Diseases, 2000, vol. 51, No. 1, pp. 31-37.
Jantet et al., Chronic Venous Insufficiency: Worldwide Results of the RELIEF Study, Angiology, 2002, vol. 53, No. 3, pp. 245-256.
Lacombe et al., Activity of Daflon 500 mg on the Hemorheological Disorders in Diabetes, International Angiology, 1989, vol. 8, Suppl to No. 4, pp. 45-48.
Libbey et al., Autistic Disorder and Viral Infections, Journal of NeuroVirology, 2005, vol. 11, pp. 1-10.
McAlonan et al., Brain Anatomy and Sensorimotor Gating in Asperger's Syndrome, Brain, 2002, vol. 127, pp. 1594-1606.
Meyer et al., The Neurodevelopmental Impact of Prenatal Infections at Different Times of Pregnancy: The Earlier the Worse?, The Neuroscientist, 2007, vol. 13, No. 3, pp. 241-256.
Murphy et al., Reciprocal Actions of Interleukin-6 and Brain-Derived Neurotrophic Factor on Rat and Mouse Primary Sensory Neurons, European Journal of Neuroscience, 2000, vol. 12, pp. 1891-1899.
Muthian et al., Quercetin, a Flavonoid Phytoestrogen, Ameliorates Experimental Allergic Encephalomyelitis by Blocking IL-12 Signaling Through JAK-STAT Pathway in T Lymphocyte, Journal of Clinical Immunology, 2004, vol. 24, No. 5, pp. 542-552.
Ornitz et al., Startle Modulation Studies in Autism, Journal of Autism and Developmental Disorders, 1993, vol. 23, No. 4, pp. 619-637.
Park et al., Green Tea Polyphenol Epigallocatechin-3-Gallate Suppresses Collagen Production and Proliferation in Keloid Fibroblasts via Inhibition of the STAT 3 Signaling Pathway, Journal of Investigative Dermatology, 2008, vol. 128, pp. 2429-2441.
Patterson, Immune Involvement in Schizophrenia and Autism: Etiology, Pathology and Animal Models, Behavioural Brain Research, 2009, vol. 204, pp. 313-321.
Radyushkin et al., Neuroligin-3-Deficient Mice: Model of a Monogenic Heritable Form of Autism with an Olfactory Deficit, Genes, Brain and Behavior, 2009, vol. 8, pp. 416-425.
Reagan-Shaw et al., Dose Translation from Animal to Human Studies Revisited, The FASEB Journal, Life Sciences Forum, 2007, vol. 22, pp. 659-661.
Silver et al., Lipopolysaccharide-Induced Fetal Death: The Role of Tumor-Necrosis Factor Alpha, Biology of Reproduction, 1994, vol. 50, pp. 1108-1112.
Wang et al., Disruption of Interleukin-18, but Not Interleukin-1, Increases Vulnerability to Preterm Delivery and Fetal Mortality after Intrauterine Inflammation, The American Journal of Pathology, 2006, vol. 169, No. 3, pp. 967-976.
Rezai-Zadeh et al., Apigenin and Luteolin Modulate Microglial Activation via Inhibition of STATI-Induced CD40 Expression, Journal of Neuroinflammation, 2008, vol. 5, pp. 41-50.
Swerdlow et al., Tactile Prepuff Inhibition of Startle in Children with Tourette's Syndrome: In Search of an "fMRI-Friendly" Startle Paradigm, Biol. Psychiatry, 2001, vol. 50, pp. 578-585.
Samuelsson et al., Prenatal Exposure to Interleukin-6 Results in Inflammatory Neurodegeneration in Hippocampus with NMDA/GABAA Dysregulation and Impaired Spatial Learning, Am. J. Physiol. Regul. Integr. Comp. Physiol., 2006, vol. 290, pp. R1345-R1356.
Tan et al., CD40 is Expressed and Functional on Neuronal Cells, The EMBO Journal, 2002, vol. 21, No. 4, pp. 643-652.
Siddiquee et al., Selective Chemical Probe Inhibitor of STAT3, Identified Through Structure-Based Virtual Screening, Induces Antitumor Activity, PNAS, 2007, vol. 104, No. 18, pp. 7391-7396.
Turner, Annotation: Repetitive Behaviour in Autism: A Review of Psychological Research, J. Child Psychol. Psychiat., 1999, vol. 40, No. 6, pp. 839-849.
De Martino et al., Interleukin-6 Release by Cultural Peripheral Blood Mononuclear Cells Inversely Correlates with Height Velocity, Bone Age, Insulin-like Growth Factor-I, and Insulin-like Growth Factor Binding Protein-3 Serum Levels in Children with Perinatal HIV-1 Infection, Clinical Immunology, 2000, vol. 94, No. 3, pp. 212-218.
Di Domenico et al., Involvement of STAT3 in Mouse Brain Development and Sexual Dimorphism: A Proteomics Approach, Brain Research, 2010, vol. 1362, pp. 1-12.
Riikonen et al., Cerebrospinal Fluid Insulin-like Growth Factors IGF-1 and IGF-2 in Infantile Autism, Developmental Medicine and Child Neurology, 2006, vol. 48, pp. 751-755.
Fowden, The Insulin-like Growth Factors and Feto-Placental Growth, Placenta, 2003, vol. 24, pp. 803-812.
Acosta et al., Imaging Data in Autism: From Structure to Malfunction, Seminars in Pediatric Neurology, 2004, vol. 11, pp. 205-213.
Dore et al., Rediscovering an Old Friend, IGF-I: Potential Use in the Treatment of Neurodegenerative Diseases, Trends Neurosci., 1997, vol. 20, No. 8, pp. 326-331.
International Search Report for PCT/US2009/062753 dated Apr. 21, 2010.
Pecking, B. Fevrier, C. Wargon and G. Pillion, Efficacy of Daflon 500 mg in the treatment of lymphedema (secondary to conventional therapy of breast cancer), Angiology 48(1) (1997), pp. 93-98.
P.M. Rodier, Chronology of neuron development: animal studies and their clinical implications, Dev. Med. Child Neurol. 22 (1980), pp. 525-545.
Careaga M, Van de Water J, Ashwood P., Immune dysfunction in autism: A pathway to treatment, Neurotherapeutics: The Journal of the American Society for Experimental NeuroTherapeutics. Jul. 2010;7(3):283-92.
Lazarus DD, Moldawer LL, Lowry SF., Insulin-like growth factor-1 activity is inhibited by interleukin-1alpha, tumor necrosis factor-alpha, and interleukin-6, Lymphokine and Cytokine Res. Aug. 1993;12(4):219-23.
Hansen-Pupp I, Hellström-Westas L, Cilio CM, Andersson S, Fellman V, Ley D., Inflammation at birth and the insulin-like growth factor system in very preterm infants, Acta Paediatr. Jun. 2007;96(6):830-6.
Meyer OC (1994). Safety and security of daflon 500 mg in venous insufficiency and in hemorrhoidal disease, Angiology 45(6)Part 2: 579-584.
Ogata A, Chauhan D, Teoh G, Treon SP, Urashima M, Schlossman RL, Anderson KC., IL-6 triggers cell growth via the Ras-dependent mitogen-activated protein kinase cascade, J Immunol. Sep. 1, 1997;159(5):2212-21.
Smith et al., Maternal immune activation alters fetal brain development through interleukin-6, Journal of Neuroscience. 2007 27(40): 10695-10702.
Rice-Evans C, Packer L (1998) Nutritional Studies of Flavonoids in Wine, Flavonoids in Health and Diseases, eds Rice-Evans C, Packer L (CRC, Boca Raton, FL), pp. 329-395.

\* cited by examiner

LUTEOLIN AND DIOSMIN/DIOSMETIN AS NOVEL STAT3 INHIBITORS FOR TREATING AUTISM

CROSS REFERENCE TO RELATED APPLICATIONS

This application is a continuation of currently pending U.S. patent application Ser. No. 13/093,401, entitled, "Luteolin and Diosmin/Diosmetin as Novel STAT3 Inhibitors for Treating Autism", filed Apr. 25, 2011, which claims priority to prior filed International Application, Serial Number PCT/US2009/062753, entitled, "Luteolin and Diosmin/Diosmetin as Novel STAT3 Inhibitors for Treating Autism" filed Oct. 30, 2009, which claims priority to U.S. Provisional Patent Application Ser. No. 61/109,538 entitled, "Luteolin and Diosmin/Diosmetin as Novel STAT3 (Signal Transducer and Activator of Transcription) Inhibitors for Treating Autism", filed Oct. 30, 2008, each of which are herein incorporated by reference.

FIELD OF INVENTION

The present invention relates to compositions and methods for the screening and treatment of autoimmune disorders such as autism, schizophrenia, and type 1 diabetes. Specifically this invention uses flavonoids to inhibit the activation/phosphorylation of STAT3 induced by IL-6.

BACKGROUND OF THE INVENTION

Autism is a brain disorder that begins in early childhood and persists throughout adulthood. It affects three crucial areas of development: communication, social interaction, and creative or imaginative play. Children with autism have difficulties in social interaction and communication and may show repetitive behaviors and have unusual attachments to objects or routines. Similar to other neuropsychiatric disorders, the mechanism(s) involved in autism development have yet to be fully determined. Studies have indicated brain development in autism is abnormally characterized by accelerated growth in early life that results in brain enlargement in childhood (Aylward et al., 2002; Courchesne et al., 2001; Tate et al. 2007). Accelerated brain growth is also a feature of acquired macrocephaly, a finding in many autistic children. Also along these lines, a positive association between increasing radiate white matter volume and motor skill impairment in children with autism has also been shown (Mostofsky et al. 2007). Although such results are not universal for all autistic patients, they do define a significant subgroup of affected patients (Acosta and Pearl 2004; Ben Bashat et al. 2007), which potentially could be spared disease if intervention could be made early in neurodevelopment.

Autism affects thousands of Americans and encompasses a number of subtypes, with various putative causes and few documented ameliorative treatments. The disorders of the autistic spectrum may be present at birth, or may have later onset, for example, at ages two or three. Autism has increased tenfold in the last fifteen years. It is estimated to afflict between 2 and 5 of every 1000 children and is four times more likely to strike boys than girls. It is estimated that about 1.5 million American children and adults have autism. The U.S. Department of Education has estimated the rate of autism is increasing at 10 to 17 percent each year.

Autism has a strong genetic component, and in some families, autism tends to be more prevalent. In identical twins with autism both are usually affected. However, the number of children with autism appears to be increasing more than expected for a genetic disorder. This suggests to scientists that genetic abnormalities require the influence of other factors to cause the disorder.

The main goals of treatment are to lessen associated deficits and family distress, and to increase quality of life and functional independence. No single treatment is best and treatment is typically tailored to the child's needs. Although there is no cure for autism, clinicians do agree that early detection could significantly improve chances in if not preventing it, then at last reducing its weakening effects. Current treatments were shown efficacious when applied earlier in child's life, prior to the full blown onset. Thus the early prognosis is a vital component in the fight against this disease.

IL-6 and JAK2/STAT3

Inflammation plays a key role in many neurological diseases as well as in neurodegenerative diseases displaying cognitive and behavioral impairments. Recent studies have shown that abnormal immune responses contribute to autistic pathogenesis in animals (Warren et al., 2005). Neuroglia inflammation has been observed in the brain tissue of autistic individuals from as young as 5 to as old as 45 (Honda, Michelle (2008) *Flavonoids benefit oxidative stress and inflammation associated with autism*, www.MichelleHonda.com) Studies have been conducted that show that autistic brains show evidence of inflammation in certain brain areas, most prominently in the cerebellum. Ongoing inflammation was also found in the fluid surrounding the brain and spinal cord (Vargas D. L., et al. (2004) *Neuroglial activation and neuroinflammation in the brain of patients with autism*, Annals of Neurology 57:67-81).

Sharp increases in IL-6 production have been shown under inflammatory conditions in the brain. The main sources of IL-6 are reactive astrocytes and microglia (Behrens, M. M. et al. (2008) *Interleukin-6 mediates the increase in NADPH-oxidase in ketamine model of schizophrenia*, The Journal of Neuroscience, 28(51):13957-13966). Interleukin 6 (IL-6) plays a key role in developing autistic phenotype in the mice (Smith et al., 2007). It is well known that IL-6 highly activates signal transducer and activator of transcription protein 3 (STAT3) signal pathway in vitro and in vivo (Ebong et al., 2004; Ogata et al., 1997). The binding of IL-6 to its receptor (IL-6R) generates a complex with the gp130 protein thus triggering activation of Janus-activated kinases (JAK). This is then critical for inducing phosphorylation of docking sites of the receptor for SHP2 (SH2 domain-containing tyrosine phosphatase) and STAT (signal transducers and activators of transcription) proteins (Heinrich et al., 1998). There are various STAT protein variants, which cause an array of signaling which can result in neuronal death (Giunta et al., 2006, 2007, & 2008) or growth/differentiation (Kamimura et al., 2003). Phosphorylated STAT3 molecules dimerize and then move to the nucleus, where they lead to transactivation of target genes largely associated with neuronal growth (Schindler & Darnell 1995).

JAK2/STAT3 pathways induced by IL-6 play a crucial role in cell proliferation, a phenomenon known to occur at excess levels in the brains of a significant proportion of autistic children. Various studies demonstrate IL-6 signaling through Stat3 modulates the growth and proliferation of both neurons directly or via inhibition of neuron death. In vitro, stimulated astrocytes and microglia produce IL-6 (Van Wagoner et al., 1999; John et al., 2003), and its chimeric derivatives rescue neurons preserve myelin basic protein production in hippocampal slices exposed to excitotoxic insult (Pizzi et al., 2004). IL-6 also supports the survival of cultured postnatal rat septal cholinergic neurons (Hamma et al., 1999). Moreover, IL-6 has been shown to be crucially involved in the development, differentiation, regeneration, and degeneration of neurons in the peripheral and central nervous system (Gadient & Otten, 1994 & 1997). Further, evidence to support IL-6/Stat3 mediated growth signaling was demonstrated in spinal cord-derived neural progenitor cells (NPCs) exposed to IL-6 and epidermal growth factor (EGF). The phosphorylation level of Jak2/Stat3 was determined and maximal phosphorylation occurred at 30 minutes of NPCs exposure to IL-6. In addition, phosphorylation of Jak2/Stat3 was attenuated by pre-treatment of cells with AG490, the JAK2 specific inhibitor, suggesting that this pathway play a key in repopulation and regeneration of spinal cord tissue after injury (Kang et al., 2008).

Maternal Infection Activation

The earliest point in neurodevelopment is fetal. During the neurodevelopment stage, it has been reported that activation/regulation of STAT3 signal pathways is critically involved (Yvonne et al. 2000). Maternal infection increases the risk of fetal neurological injury. Systemic inflammatory response during pregnancy may contribute to neuropsychiatric disease in childhood and adulthood (Huleihel et al., 2004). Epidemiological studies have shown that the risk of developing autism is associated with prenatal maternal infection. This presumably results from neurodevelopmental defects triggered by cytokine-related inflammatory events (Ashdown et al., 2006; Meyer et al., 2008), as there is increased incidence of autism in the offspring of mothers who suffered infections while pregnant (Patterson, 2005). Because of the strong genetic component in autism, it is likely that only genetically susceptible individuals who were exposed to maternal infection would develop the disorder. Thus, it has been suggested that the risk of autism associated with maternal infection may be considerably more than three to seven-fold in susceptible individuals.

Several studies suggest the maternal immune response or "activation" to infection, rather than infection of the fetus itself (Shi et al., 2003 & 2005), is responsible for the increased incidence of autism in the offspring of mothers who suffered infections while pregnant. After maternal immune activation (MIA) by influenza, LPS, or poly(I:C), cytokine levels are altered in the maternal serum as well as the amniotic fluid, placenta, and, most importantly, the fetal brain (Fidel et al., 1994; Cai et al., 2000; Urakubo et al., 2001; Gayle et al., 2004; Paintlia et al., 2004; Gilmore et al., 2005; Beloosesky et al., 2006; Meyer et al., 2006). Cytokines were initially characterized as compounds of the immune response, but have since been found to play a much broader, diverse role in physiology. Cytokines, including interleukin-6 (IL-6), IL-11, IL-27 and leukemia inhibitory factor, have been shown to confer signaling in both the developing and adult brain; both directly and indirectly modulating neuronal functions (Bauer et al., 2007). Therefore, it is not surprising that inflammatory cytokines and their receptors modulate brain morphology during development as well. Particularly, IL-6 is likely a central link between maternal infection and neurodevelopmental derangement (Akira et al., 1990; Smith et al., 2007).

Maternal MIA in pregnant rodents yields offspring with abnormalities in behavior, histology, and gene expression that mimic psychiatric features of autism. This suggests MIA as a useful model of the development of autism. Specifically, single maternal injection of IL-6 on day 12.5 of pregnancy caused prepulse inhibition (PPI) and latent inhibition (LI) deficits in adult offspring. Co-administration of anti-IL-6 in the poly (I:C) model of MIA prevented the PPI, LI, and exploratory and social deficits caused by poly(I:C) and normalized the associated changes in gene expression in the brains of the adult offspring. Most convincingly, MIA in IL-6 knock-out mice did not yield several of the behavioral changes observed in the offspring of wild-type mice after MIA.

MIA-induced cytokines confer both direct and indirect effects on the fetus. Two methods have been used to study these effects: injecting or up-regulating cytokines during pregnancy in the absence of MIA, or blocking endogenous cytokines or preventing their induction during MIA. A study of the role of TNF-α in LPS-induced fetal loss and growth restriction indicated injection of anti-TNF-α antibodies or an inhibitor of TNF-α synthesis [pentoxifylline] can reduce these effects of LPS. Conversely, injection of TNF-α alone can induce fetal loss (Siler et al., 1994 and Xu et al., 2006) which is significantly worse in IL-18 knockout mice, but not in IL-1α/β knockout mice (Wang et al., 2006).

Much of the previous investigations of cytokine mediation of MIA effects on neuropathology and behavior in the offspring have focused on IL-6. This cytokine is involved in the regulation of physiological processes including inflammation and neurodevelopment; making it a particularly appealing candidate molecule for MIA-induced neuropathology. Indeed, during neurodevelopment, the signal transducer and activator of transcription-3 (STAT3) pathway, activated by IL-6, maintains homeostasis between neuro- and gliogenesis (He et al., 2005 and Murphy et al., 2000).

In support, Samuelsson et al., 2006 intraperitoneally injected IL-6 in pregnant rats for 3 days resulting in severe effects on the offspring. An important finding was that IL-6 mRNA levels remain elevated in the hippocampi of the offspring at 4 and 24 weeks of age; indicative of the ongoing state of immune dysregulation in adult autistic brains. Spatial memory in the water maze, a hippocampal-dependent behavior, was observed in that study. Importantly, the IL-6-treated offspring displayed increased latency to escape and time spent near the pool wall. Therefore, prolonged exposure to elevated IL-6 in utero causes a deficit in working memory (for reviews see Patterson 2008).

Blocking endogenous IL-6 in MIA also supports the central role of this cytokine (Smith et al., 2007). Co-injection of anti-IL-6 antibody with maternal poly(I:C) blocks the effects of MIA on the behavior of the offspring. Further, maternal injection of poly(I:C) in an IL-6 knockout mouse results in normal behaving offspring. In addition, the anti-IL-6 antibody also blocks the changes in brain transcription induced by maternal poly(I:C) (Patterson 2008). Maternal injection of poly(I:C) induces expression of IL-6 mRNA in fetal brain and placenta, and this is also dependent on the IL-6 induced by maternal poly(I:C) (Patterson 2008) (E. Hsiao and P. H. Patterson, unpublished). Taken together these previous works by other groups indicate both direct and indirect (positive feedback loop) mechanisms for IL-6 mediated MIA in the context of aberrant fetal brain development which could lead to an autism-like phenotype (Patterson 2008).

Schizophrenia

IL-6 plays a role not only in the pathogenesis of autism but also in the pathogenesis of schizophrenia in the context of maternal immune activation. MIA is used to describe an increase in circulating maternal cytokines in response to an infection during pregnancy (Smith et al., 2007). The ensuing cytokine response and the highly susceptible developmental period in which it occurs may precipitate the neuropathological and behavioral deficits observed in autism and related disorders such as schizophrenia. Schizophrenia and autism can result from the interaction between a susceptibility genotype and environmental risk factors. IL-6 is critical for mediating the behavioral and transcriptional changes in offspring in which mothers were exposed to infection. There is evidence to indicate that the maternal immune response, as opposed to the direct infection of the fetus, is responsible for the increased incidence of schizophrenia and autism in the offspring of mothers who suffer infections during pregnancy (Smith et al., 2007).

Neuroprotection IL-6/STAT3 signaling against N-methyl-D-aspartate (NMDA)-induced neurotoxicity has also been demonstrated. Cultured cerebellar granule neurons (CGNs) from postnatal (eight-day) infant rats were chronically exposed to IL-6 for eight days, and then NMDA (100 mol/L) was administered to the cultured CGNs. By way of MTT, and TUNEL assays, as well as confocal laser scanning microscope (CLSM) and western blotting, it was shown that NMDA stimulation of cell death could be avoided by IL-6 treatment. The NMDA stimulation of the CGNs chronically pretreated with IL-6 caused a very large increase in neuronal vitality, as well suppression of neuronal apoptosis compared with that in the control neurons without IL-6 pretreatment. The levels of phospho-Stat3 are significantly higher in IL-6-pretreated CGNs than those in IL-6-untreated neurons. Ketamine is an NMDA receptor antagonist which produces psychosis in humans and exacerbates symptoms in schizophrenic patients. Ketamine has been shown to activate the innate immune enzyme NADPH-oxidase in the brain. IL-6 has been shown to be the downstream mediator of ketamine in the induction of Nox2 and to activate NADPH oxidase in the brain providing further evidence for the role of IL-6 in the pathogenesis of schizophrenia (Behrens et al. 2008).

Diabetes

There is also an interaction between IL-6 and insulin systems, specifically insulin-like growth factor-1 (IGF-1) (Venkatasubramanian, G. (2007) *Pathogenesis of Schizophrenia & Autism: The Interaction between Interleukin and Insulin Systems*, Journal of Neuroscience 27(40): 10695-10702). IGF-1 has a significant role in fetal development and has neuroprotective, anti-apoptotic properties that are crucial for the optimal development of the brain (Fowden, 2003; Dore et al., 1997). IL-6 inhibits the secretion and biological activity of IGF-1 (de Martino et al., 2000; Lazarus et al., 1993). Cerebral damage in fetal pro-inflammatory states is associated with high IL-6 and low IGF-1 levels (Hansen-Pupp et al., 2007). Elevated IL-6 and decreased IGF-1 levels are also shown in schizophrenia and autism (Potvin et al., 2007; Venkatasubramanian et al., 2007; Jyonouchi et al., 2001; Riikonen et al., 2006).

Patients with diabetes also have reduced serum levels of IGF-1 that occur in response to a state of insulin resistance. IGF-1 acts in concert with insulin and has an important role in maintaining glucose homeostasis and protein metabolism in type 1 diabetes (Simpson, H. L. et al. (2004) *Insulin-like growth factor has a direct effect on glucose and protein metabolism, but no effect on lipid metabolism in type 1 diabetes*, The Journal of Clinical Endocrinology & Metabolism 89(1):425-432). In addition, similarly to the levels shown in schizophrenia and autism, patients exhibiting insulin-resistant states such as in diabetes have been shown to have increased levels of IL-6 and decreased levels of IGF-1 (Glund, S. et al. (2007) *Interleukin-6 directly increases glucose metabolism in resting human skeletal muscle*, The Journal of the American Diabetes Association 56(6):1630-1637).

Flavonoids

Flavonoids, plant polyphenolic compounds abundant in fruits and vegetables, exhibit a wide variety of biological effects, including antioxidant free-radical scavenging and anti-inflammatory properties (Rice-Evans C, Packer L (1998) in *Flavonoids in Health and Diseases*, eds Rice-Evans C, Packer L (CRC, Boca Raton, Fla.), pp 329-395). The flavonoid luteolin (3',4',5,7-tetrahydroxyflavone), abundant in celery, green pepper, parsley, perilla leaf, and chamomile tea (Shimoi K, et al. (1998) *Intestinal absorption of luteolin and luteolin 7-O-β-glucoside ire rats and humans. FIBS Lett* 438: 220-224), is of particular interest for modulating immune reactions as several studies comparing the anti-inflammatory properties of luteolin with other flavonoids such as quercetin, genistein, or hesperetin in peripheral macrophages found luteolin to be most potent (Xagorari A, et al. (2001) *Luteolin inhibits an endotoxin-stimulated phosphorylation cascade and proinflammatory cytokine production in macrophages. J Pharmacol Exp Ther* 296:181-187; Comalada. M, et al. (2006) *Inhibition of proinflammatory markers in primary bone marrow-derived mouse macrophages by naturally occurring flavonoids: Analysis of the structure-activity relationship. Biochem Pharmacol* 72:1010-1021).

Luteolin has been shown to inhibit LPS-induced NF-κB transcriptional activity in intestinal epithelial cells, mouse bone-marrow derived dendritic cells (Kim J S, Jobin C (2005) *The flavonoid luteolin prevents lipopolysaccharide-induced NF-κB signaling and gene expression by blocking IκB kinase activity in intestinal epithelial cells and bone-marrow derived dendritic cells. Immunology* 115:375-387), murine macrophage cells, and rat fibroblasts (Kim S H, et al (2003) *Luteolin inhibits the nuclear factor-κB transcriptional activity in Rat-1 fibroblasts. Biochem. Pharmacol* 66:955-963). In another study, luteolin inhibited LPS-stimulated TNF-α and IL-6 in a murine macrophage cell line. These studies suggest luteolin modulates cell signaling pathways activated by LPS and subsequent production of inflammatory cytokines.

Diosmin containing supplements have been in use in Europe for the past three decades. Diosmin is currently considered a vascular-protecting agent and has been used safely for treatment of chronic venous insufficiency/varicose veins, hemorrhoids, lymphedema, and diabetes (Le Lyseng-Williamson and Perry 2003; Mlakar and Kosorok 2005; Nicolaides 2005). Clinical trials have used doses of 500-2,000 mg per day orally for up to one year. Throughout these trials, diosmin demonstrated an excellent safety profile and were well tolerated. Adverse events with such complexes were rare; and when they occurred, they were always mild, and transient. The side effects typically observed were mild cases of digestive intolerance requiring no changes in treatment.

Pharmacokinetic studies demonstrated diosmin is rapidly transformed in the intestine to diosmetin, its aglycone form (Cova et al., 1992; Labrid 1994; Meyer 1994). Diosmetin is subsequently absorbed and distributed throughout the body with a plasma half-life of 26-43 hrs. Data from this study was used to help determine the shape of the dose response, and optimal dose for human clinical trials to test diosmin as an effective anti-Stat3 prenatal supplement in infected, or potentially infected pregnant mothers. Diosmin can be used as a prenatal supplement to defend against autism risk, just as folate is currently used as prophylaxis against neural tube defects in human offspring.

Park et al., 2008 found that EGCG inhibits STAT3 activation as an integral part of inhibition of keloid formation. In an earlier study it was found that silibinin, a flavonoid, inhibits constitutive activation of STAT3, and causes caspase activation and apoptotic death of human prostate carcinoma cells (Agarwal et al., 2007). Prior to this, it was demonstrated that in vivo treatment of SJL/J mice with quercetin, a flavonoid, (i.p. 50 or 100 μg every other day which is equal to 1.25 mg/kg/day or 2.5 mg/kg/day) ameliorates experimental autoimmune encephalitis (EAE) by inhibiting IL-12 production and neural antigen-specific Th1 differentiation. In vitro treatment of activated T cells with this same flavonoid quartering blocks IL-12-induced tyrosine phosphorylation of JAK2, TYK2, STAT3, and STAT4, yielding a reduced IL-12-induced T cell proliferation and Th1 differentiation (Muthian and Bright 2004).

Our studies indicated that IL-6 activates the JAK2/STAT3 pathway, as N2a neuronal cells and brain homogenates from newborn IL-6-induced MIA (IL-6/MIA) offspring showed increased neuronal JAK2/STAT3 phosphorylation. In adulthood, these mice showed deficits in social interaction, suggesting that not only does IL-6 activate the JAK2/STAT3 pathway, but that it is also involved in the abnormal behavioral pathologies observed in MIA offspring and autism and related disorders. Next we investigated if inhibition of JAK2/STAT3 signaling could attenuate MIA-induced pathologies. Previous research by our laboratory has shown that bioflavonoids such as epi-gallocatechin gallate (EGCG) or luteolin, inhibit IFN-γ induced STAT1 activation and attenuate production of pro-inflammatory cytokines in cultured and primary microglial cells (Giunta et al., 2006, Jagtap et al., 2009 and Rezai-Zadeh et al., 2008).

We investigated the prophylactic effects of two flavonoids which possess better bioavailability and safety than these previously tested compounds. These two flavonoids are, luteolin, and its structural analog, diosmin. We found that JAK2/STAT3 phosphorylation and signaling as well as behavioral abnormalities in IL-6 induced MIA offspring could be ameliorated with these naturally occurring compounds. Our results showed that administration of diosmin (10 mg/kg/day) was able to block the STAT3 signal pathway; significantly opposing IL-6-induced abnormal behavior and neuropathological abnormalities in MIA/adult offspring. Using guidelines put forth by the Food and Drug Administration (Reagan-Shaw et al., 2008), this 10 mg/kg/day dose in mice is equivalent to 0.81 mg/kg/day in humans which translates into 48.6 mg/day for a 60 kg person.

The present invention includes methods for the treatment of autoimmune disorders such as autism, schizophrenia, and diabetes through the administration of flavonoids. Flavonoids, luteolin, diosmin, and its aglycone form, diosmetin, were found to inhibit activation/phosphorylation of STAT3 induced by IL-6 in cultured neuronal cells. These flavonoids have a profound and dose-dependent effect on inhibiting STAT3 activation using PC12 and N2a cells as evidenced by markedly decreased STAT3 phosphorylation by Western Blot Analysis. This effect is mediated by a reduction in downstream productions of the STAT3 signal pathway. Pregnant mice (E4) were treated with diosmin in the presence or absence of mouse IL-6 and autistic phenotypes, including pathology and behavioral changes in these treated mice, and were compared with a control. It was found that diosmin attenuates IL-6-induced autistic phenotype in mice. Due to the nature of these compounds, they are also effective in treating other diseases including schizophrenia and diabetes.

SUMMARY OF THE INVENTION

An illustrative embodiment of the present invention includes a method of treating an autoimmune disorder such as autism, schizophrenia, or diabetes through the administration of a therapeutically effective amount of a flavonoid. The flavonoid is preferably luteolin, diosmin, or diosmetin or any of their structural analogues or derivatives.

The flavonoid is preferably administered orally. The flavonoid can be administered at 25 mg, 50 mg, 100 mg, 200 mg, 400 mg, 600 mg, 800 mg, 1000 mg, 1200 mg, 1400 mg, 1600 mg, 1800 mg, and 2000 mg. The maximum dosage can be 2000 mg. The dosage can be weight dependent. The dosage administered can be between 0.81 mg/kg/day and 2.5 mg/kg/day. The preferred dose of the flavonoid is at least 0.81 mg/kg/day.

In another embodiment, the present invention includes a method of treating autism through the administration of a therapeutically effective amount of a flavonoid such as luteolin, diosmin, or diosmetin.

An additional embodiment includes a method of reducing inflammation due to an autoimmune disease such as autism, schizophrenia, or diabetes through the administration of a flavonoid. The flavonoid may be luteolin, diosmin, or diosmetin. Preferably the flavonoid is administered orally and the preferred dose is at least 0.81 mg/kg/day.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Throughout this application various publications are referenced. Disclosures of these publications in their entireties are hereby incorporated by reference into this application in order to more fully describe the state of the art to which this invention pertains.

The "therapeutically effective amount" for purposes herein is thus determined by such considerations as are known in the art. A therapeutically effective amount of the flavonoids such as luteolin, diosmin, or diosmetin, their analogues or any combination thereof is that amount necessary to provide a therapeutically effective result in vivo. A therapeutically effective result refers to a dose of the flavonoid that is sufficient to provide a physical benefit or a therapeutic benefit. The amount of flavonoids such as luteolin, diosmin, or diosmetin or any combination thereof must be effective to achieve a response, including but not limited to total prevention of (e.g., protection against) and to improved survival rate or more rapid recovery, or improvement or elimination of symptoms associated with inflammatory disorders, autoimmune disorders, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The term "administration" or "administering" as used throughout the specification to describe the process in which a flavonoid is delivered to a patient for treatment purposes. This includes parenternal; intraventricular; intraparenchymal; including spinal cord and brain stem; intracisternal; intrastriatal; intranigral; orally; rectally; and other routes that allow the flavonoid to contact cells. The term "parenternal" refers to subcutaneous, intracutaneous, intravenous, intramuscular, intrathecal, intralesional, intraartricular, intraarterial, intrasynovial, intrasternal, intrathecal, and intracranial injection, as well as various infusion techniques. The flavonoid may be administered independently or in combination with other compounds. Administration will often depend on the disease and level of progression.

The term "autoimmune disorder" as used throughout refers to those disease states and conditions wherein the immune response of the patient is directed against the patient's own constituents, resulting in an undesirable and often terribly debilitating condition. As used herein, "autoimmune disorder" is intended to further include autoimmune conditions, syndromes, and the like.

The term "flavonoid" is used throughout the specification to identify those polyphenolic compounds that are ubiquitous in nature. The term "flavonoid" as used herein includes isoflavones, anthocyanidins, flavans, flavonols, flavones, citrus flavonoids, hesperidin, chalcones, catechins, rutin, and flavanones.

We have found that the flavonoids, luteolin and diosmin/diosmetin, have a profound and dose-dependent effect on inhibiting STAT3 activation using PC12 and N2a cells, as evidenced by markedly decreased STAT3 phosphorylation on a Western blot analysis. Most importantly, this effect is mediated by a reduction in downstream productions of STAT3 signal pathway.

We have shown that the citrus bioflavonoid luteolin inhibits Stat3 phosphorylation in both murine neuron-like cells and primary neuronal cells challenged with IL-6. Diosmin (a glycoside of a structurally similar flavanoid to luteolin), administered orally, significantly changes behavioral deficits in social interaction in IL-6/MIA adult offspring. Additionally, diosmin reduces the CNS levels in pro-inflammatory cytokines consistent with Jak2/Stat3 signal pathway inhibition.

Preliminary studies showed that the citrus bioflavonoid, luteolin, inhibits neuronal Jak2/Stat3 phosphorylation in both murine neuron-like (N2a) cells and primary cultured neuronal cells challenged with IL-6. As a validation of these findings, the effects of a Stat3 inhibitor (S31-201) and diosmin, a flavanoid structurally similar to luteolin, was examined on Jak2/Stat3 signaling. When either agent was applied to pregnant mice with an injection of IL-6 to induce MIA, Jak2/Stat3 phosphorylation and pro-inflammatory cytokines were both significantly reduced in brain homogenates from newborn mice. It was also found that diosmin administered orally in chow (10 mg/kg/day) significantly changes behavioral deficits in social interaction and reduces pro-inflammatory cytokines in brain tissues of IL-6/MIA adult offspring. Finally, it was demonstrated that diosmin reduces CNS levels of pro-inflammatory cytokines consistent with Jak2/Stat3 signal pathway inhibition.

Methods

Reagents

Luteolin (>95% purity by HPLC) was purchased from Sigma (St Louis, Mo., USA). Diosmin (>90% purity by HPLC) was purchased from Axxora (San Diego, Calif., USA). Antibodies against JAK2, phospho-JAK2, STAT3 and phospho-STAT3 were obtained from Cell Signaling Technology (Danvers, Mass., USA). ELISA kits for tumor necrosis factor-α (TNF-α) and Interleukin-1β (IL-1β) were obtained from R&D Systems (Minneapolis, Minn., USA). BCA protein assay kit was purchased from Pierce Biotechnology (Rockford, Ill., USA). Murine recombinant IL-6 was purchased from eBioscience (San Diego, Calif., USA).

Primary Cell Culture

Cerebral cortices were isolated from C57BL/6 mouse embryos, between 15 and 17 days in utero. After 15 min of incubation in trypsin (0.25%) at 37° C., individual cortices were mechanically dissociated. Cells were collected after centrifugation at 1200 rpm, resuspended in DMEM supplemented with 10% fetal calf serum, 10% horse serum, uridine (33.6 g/mL; Sigma) and fluorodeoxyuridine (13.6 g/mL; Sigma), and plated in 24 well collagen coated culture plates at a density of $2.5 \times 10^5$ cells per well.

N2a (murine neuroblastoma) cells, purchased from the American Type Culture Collection (ATCC, Manassas, Va.) were grown in complete EMEM supplemented with 10% fetal calf serum. Cells were plated in 24 well collagen coating culture plates at a density of $1 \times 10^5$ cells per well. After overnight incubation, N2a cells were incubated in neurobasal media supplemented with 3 mM dibutyryl cAMP in preparation for treatment.

Cells were treated with 50 ng/mL murine recombinant IL-6 for a range of time points (0, 15, 30, 45, 60 or 75 min) in the presence or absence of various concentrations of luteolin (0, 1.25, 2.5, 5, 10, 20 µM) for 30 min.

Mice

Pregnant C57BL/6 mice, embryonic day 2 (E2) were obtained from Jackson Laboratory (Bar Harbor, Mass.) and individually housed and maintained in an animal facility of the University of South Florida (USF). All subsequent experiments were performed in compliance with protocols approved by the USF Institutional Animal Care and Use Committee. At E12.5, mice were intraperitoneally (i.p.) challenged (one time only) with murine recombinant IL-6 (5 µg dissolved in 200 µL of PBS/mouse) in the presence or absence of the STAT3 inhibitor S31-201 (4 µg dissolved in 200 µL of PBS/mouse) and/or treated with diosmin, administered orally (10 mg/kg/day, 0.005% in NIH31 chow). Intraperitoneal PBS injection (200 µL) was used as the control for IL-6 administration.

Western Blot

Cultured cells were lysed in ice-cold lysis buffer (20 mM Tris, pH 7.5, 150 mM NaCl, 1 mM EDTA, 1 mM EGTA, 1% v/v Triton X-100, 2.5 mM sodium pyrophosphate, 1 mM β-glycerolphosphate, 1 mM $Na_3VO_4$, 1 µg/mL leupeptin, 1 mM PMSF) as described previously (Tan et al. 2002). Mouse brains were isolated under sterile conditions on ice and placed in ice-cold lysis buffer. Brains were then sonicated on ice for approximately 3 min, allowed to stand for 15 min at 4° C., then centrifuged at 15,000 rpm for 15 min at 4° C. Total protein content was estimated using the BCA protein assay (Pierce Biotechnology) and aliquots corresponding to 100 µg of total protein were electrophoretically separated using 10% Tris gels. Electrophoresed proteins were then transferred to nitrocellulose membranes (Bio-Rad, Richmond, Calif.), washed in Tris buffered saline with 0.1% Tween-20 (TBS/T), and blocked for 1 h at ambient temperature in TBS/T containing 5% (w/v) non-fat dry milk. After blocking, membranes were hybridized overnight at 4° C. with various primary antibodies. Membranes were then washed 3× for 5 min each in TBS/T and incubated for 1 h at ambient temperature with the appropriate HRP-conjugated secondary antibody (1:1000, Pierce Biotechnology). Primary antibodies were diluted in TBS/T containing 5% BSA and secondary antibodies in TBS containing 5% (w/v) of non-fat dry milk. Blots were developed using the luminol reagent (Pierce Biotechnology). Densitometric analysis was conducted using a FluorS Multiimager with Quantity One™ software (Bio-Rad, Hercules, Calif.). For phospho-STAT3 detection, membranes were probed with a phospho-Ser727 STAT3 antibody (1:1000) and stripped with stripping solution and then reprobed with antibody that recognizes total STAT3 (1:1000). Similarly for phospho-JAK2 detection, membranes were probed with phospho-JAK2 (1:1000) and stripped and reprobed for total JAK2 (1:1000).

ELISA Cytokine Analysis

Mouse brain homogenates were prepared as described above and used at a dilution of 1:10 in PBS for these assays. Brain tissue-solubilized cytokines were quantified using commercially available ELISAs that allow for detection of IL-1β, and TNF-α. Cytokine detection was carried out according to the manufacturer's instruction. Total protein content was determined as described above and data represented as pg of cytokine/mg total cellular protein for each cytokine.

Behavioral Testing

Open field (OF)—The OF behavioral analysis is a test of both locomotor activity and emotionality in rodents (Radyushkin et al. 2009). Mice were placed in a 50×50 cm white Plexiglas box brightly lit by fluorescent room lighting and six 60 W incandescent bulbs approximately 1.5 m above the box. Activity was recorded by a ceiling-mounted video camera and analyzed from digital video files either by the automated tracking capabilities of Ethovision or counted using the behavior tracker (version 1.5, www.behaviortracker.com), a software-based event-recorder. The total distance moved and numbers of entries into the center of the arena (central 17 cm square) were determined in a 10 minute session.

Social interaction (SI)—The testing apparatus consisted of a 60×40 cm Plexiglas box divided into three chambers. Mice were able to move between chambers through a small opening (6×6 cm) in the dividers. Plastic cylinders in each of the two side chambers contained the probe mice, and numerous 1 cm holes in the cylinders enabled test and probe mice to contact each other. Test mice were placed in the center chamber, with an overhead camera recording their movements. Mice were allowed 5 min of exploration time in the box, after which an unfamiliar, same-sex probe mouse from the same experimental group was placed in one of two restraining cylinders (Radyushkin et al. 2009). The Ethovision software (Noldus, Leesburg, Va.) program measured time spent in each of the three chambers, and social preference was defined as follows: (% time spent in the social chamber)−(% time spent in the opposite chamber).

Statistical Analysis

All data were normally distributed; therefore, in instances of single mean comparisons, Levene's test for equality of variances followed by t-test for independent samples was used to assess significance. In instances of multiple mean comparisons, analysis of variance (ANOVA) was used, followed by post hoc comparison using Bonferroni's method. Alpha levels were set at 0.05 for all analyses. The STATistical package for the social sciences release 10.0.5 (SPSS Inc., Chicago, Ill., USA) was used for all data analysis.

Results

Luteolin Inhibits IL-6 Induced Neuronal JAK2/STAT3 Phosphorylation

Figure 1A:
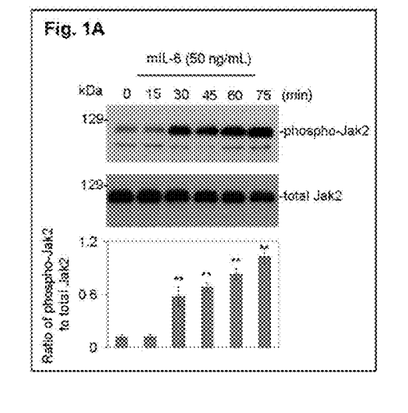
FIG. 1A is an image of a Western Blot Analysis showing that IL-6 induces Jak2 phosphorylation in cultured neuron-like cells (N2a cells). Cultured N2a cells were treated with 50 ng/mL of IL-6 for a range of time points. Cell lysates were prepared and subjected to Western Blot Analysis. Densitometry analysis shows the ratio of phosphor-Jak2 to the total Jak2. One way ANOVA showed that IL-6 significantly activates Jak2 in a time-dependent manner (**$P<0.005$).
Figure 1B:
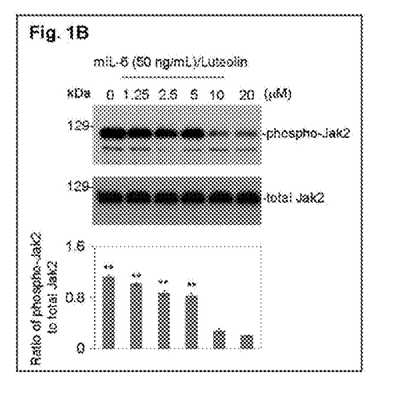
FIG. 1B is an image of a Western Blot Analysis showing that the presence of luteolin significantly inhibits IL-6-induced Jak2 phosphorylation (*$P<0.01$). Cultured Na2 cells were co-treated with IL-6 (50 ng/mL) and luteolin at various doses for 30 minutes. Cell lysates were prepared and subjected to Western Blot Analysis. Densitometry analysis reveals the ratio of phosphor-Jak2 to total Jak2.
Figure 1C:
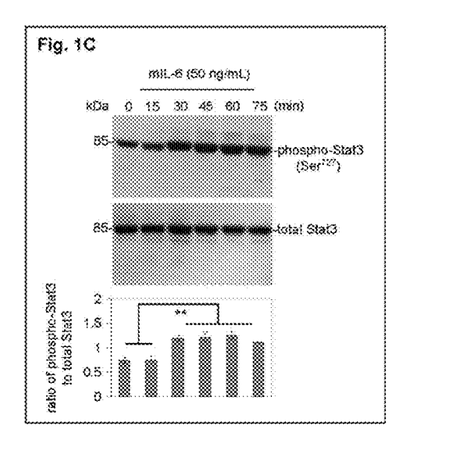
FIG. 1C is an image of a Western Blot Analysis showing that IL-6 induces STAT3 phosphorylation in cultured neuron-like cells (N2a cells). Cultured N2a cells were treated with 50 ng/mL of IL-6 for a range of time points. Cell lysates were prepared and subjected to Western Blot Analysis. Densitometry analysis shows the ratio of phosphor-STAT3 to the total STAT3. One way ANOVA showed that IL-6 significantly activates STAT3 in a time-dependent manner (**$P<0.005$).

To confirm the role of IL-6 in regulating the JAK2/STAT3 pathway, we treated murine neuron-like (N2a) cells and primary cultured neuronal cells with 50 ng/mL of murine recombinant IL-6 in a time-dependent manner. Western blot analysis of cell lysates showed that IL-6 treatment leads to a time-dependent increase in JAK2 (FIG. 1A) and STAT3 (FIG. 1C) phosphorylation. Densitometric analysis indicated significant and steady increases in JAK2 phosphorylation ($P<0.005$) beginning at 30 min and continuing until 75 min when the timed analysis was concluded (FIG. 1A). Densitometric analysis of STAT3 phosphorylation ($P<0.005$) showed a significant and maximal increase at 30 min, with no further significant increases at subsequent time points.

Figure 1D:
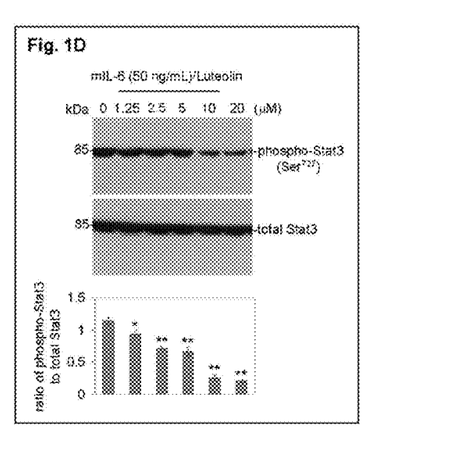
FIG. 1D is an image of a Western Blot Analysis showing that the presence of luteolin significantly inhibits IL-6-induced STAT3 phosphorylation (*$P<0.01$). Cultured Na2 cells were co-treated with IL-6 (50 ng/mL) and luteolin at various doses for 30 minutes. Cell lysates were prepared and subjected to Western Blot Analysis. Densitometry analysis reveals the ratio of phosphor-STAT3 to total STAT3. Data is representative of three independent experiments. Similar results were obtained in murine primary cultured neuronal cells using antibody specifically against phosphor-JAK2/STAT3 (Ser$^{727}$) and in N2a cells using antibody specifically against phosphor-STAT3 (Ser$^{705}$).

We next examined the effects of luteolin on IL-6 induced JAK2/STAT3 phosphorylation. Murine N2a cells and primary cultured neuronal cells were again challenged with 50 ng/mL murine recombinant IL-6 and co-treated with increasing concentrations of luteolin (0-20 μM) for 30 min. Following Western blot analysis of cell lysates, we found that luteolin reduces IL-6 induced JAK2 phosphorylation (FIG. 1B) and STAT3 phosphorylation (Ser$^{727}$) (FIG. 1D) in both murine N2a and primary neurons in a dose dependent manner with significant reductions beginning at 10 μM. Densitometric analysis showed that luteolin inhibited JAK2 and STAT3 (Ser$^{727}$) phosphorylation by almost 50% (*$P<0.01$ and **$P<0.001$, respectively). It is important to note that luteolin did not affect apoprotein levels of JAK2 or STAT3. The data shown is representative of three independent experiments. Similar results were obtained in murine primary cultured neuronal cells using antibody specifically against phospho-Jak2/Stat3 (Ser$^{727}$) and in N2a cells using antibody specifically against phospho-Stat3 (Ser$^{705}$).

Both STAT3 inhibitor, S31-201, and diosmin reduce JAK2/STAT3 phosphorylation and pro-inflammatory cytokine production in the brain tissues of IL-6/MIA newborn mice We subsequently extended the in vitro results to an animal model of MIA-induced autism by examining the effects of STAT3 inhibitor (S31-201) and diosmin (a flavonoid structural analog of luteolin), on JAK2/STAT3 phosphorylation and signaling. When either agent was co-administered to pregnant mice intraperitoneally with IL-6, JAK2/STAT3 phosphorylation and pro-inflammatory cytokine levels were both significantly reduced in the brain homogenates of newborn mice. Western blot analysis of brain homogenates shows that both S31-201 and diosmin significantly reduce IL-6 induced JAK2 (FIG. 2A) and STAT3 (FIG. 2B) phosphorylation (*$P<0.005$).

Figure 2A:
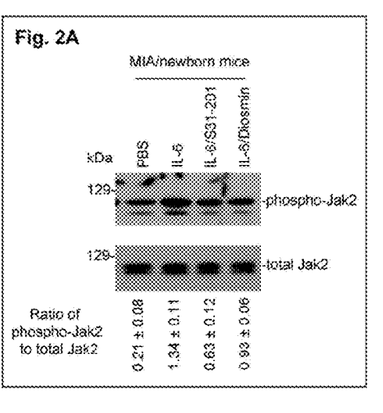
FIG. 2A is an image of a Western Blot Analysis showing both STAT3 inhibitor S31-201 and diosmin (a glycoside of a structurally similar flavonoid to luteolin) reduce Jak2 phosphorylation. Brain homogenates were prepared from newborn mice from mothers injected with IL-6, IL-6/S31-201, IL-6/diosmin, or PBS (control) and subjected to Western Blot Analysis and cytokine ELISA. Densitometry analysis shows the ratio of phospho-Jak2 to total Jak2. One way ANOVA showed that both S31-201 and diosmin significantly inhibit Jak2 signaling ($P<0.005$).
Figure 2B:
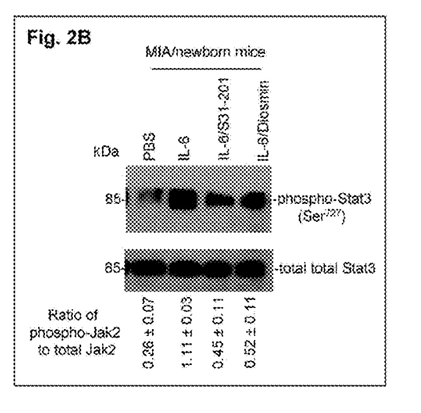
FIG. 2B is an image of a Western Blot Analysis showing both STAT3 inhibitor S31-201 and diosmin (a glycoside of a structurally similar flavonoid to luteolin) reduce STAT3 phosphorylation. Brain homogenates were prepared from newborn mice from mothers injected with IL-6, IL-6/S31-201, IL-6/diosmin, or PBS (control) and subjected to Western Blot Analysis and cytokine ELISA. Densitometry analysis shows the ratio of phospho-STAT3 to total STAT3. One way ANOVA showed that both S31-201 and diosmin significantly inhibit STAT3 signaling (P<0.005).

As shown in FIG. 2, both STAT3 inhibitor (S31-201) and diosmin (a glycoside of a structurally similar flavonoid to luteolin) reduce JAK2/STAT3 phosphorylation. Brain homogenates were prepared from newborn mice from mothers injected with IL-6, IL-6/S31-201, IL-6/diosmin or PBS (control) (n=6, 3 female/3 male) and subjected to Western blot analysis and cytokine ELISA. Most notably, the treatment of S31-201 or diosmin significantly inhibits IL-6-induced JAK2/STAT3 phosphorylation in brain tissues from newborn mice. Densitometry analysis shows the ratio of phospho-JAK2/STAT3 to total JAK2/STAT3 as indicated below the figures. One-way ANOVA showed that both significantly inhibit JAK2/STAT3 signaling ($P<0.005$).

Figure 3:
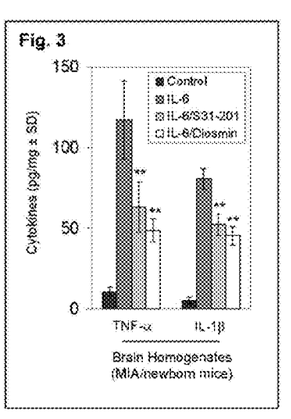
FIG. 3 is a graph showing a significant reduction of TNF- and IL1 cytokines in brain homogenates from IL-6/S31-201 and IL-6/diosmin newborn mice when compared to IL-6 only (MIA model) newborn mice (**P<0.01). Pro-inflammatory cytokine analysis by ELISA was conducted on newborn mouse brain homogenates. Data are represented as mean±SD of each cytokine in brain homogenates (pg/mg total protein) from newborn mice.

Pro-inflammatory cytokine ELISA showed significant increases in TNF-α and IL-1β levels in the brain homogenates of new born mice from IL-6 treated dams compared to those of control dams (FIG. 3). These increases were significantly reduced by almost 50% in the presence of S31-201 or diosmin (**$P<0.01$) (FIG. 3).

As shown in FIG. 3, STAT3 inhibitor (S31-201) and diosmin reduce pro-inflammatory cytokines in the brain tissues of IL-6/MIA/newborn mice. Pro-inflammatory cytokine analysis by ELISA was conducted on these newborn mouse brain homogenates. Data are represented as mean±SD of each cytokine in brain homogenates (pg/mg total protein) from these newborn mice. Analysis of results revealed a significant reduction of TNF-α and IL-1β cytokines in brain homogenates from IL-6/S31-201 and IL-6/Diosmin/newborn mice when compared to IL-6 only (MIA model) newborn mice (**$P<0.01$).

Maternally blocking the STAT3 signal pathway with the STAT3 inhibitor, S31-201 or diosmin opposes IL-6-induced abnormal behavior in MIA/adult offspring We next determined whether diosmin would attenuate behavioral abnormalities observed in the adult offspring of IL-6 treated dams. Pregnant mice were treated one time with 5 μg/mL IL-6 in the presence or absence of S31-201 (4 μg/mL) or diosmin (10 mg/kg/day diosmin) administered orally in chow. We also treated control mice (non-IL-6 treated) with the STAT3 inhibitor, S31.

Figure 4A:
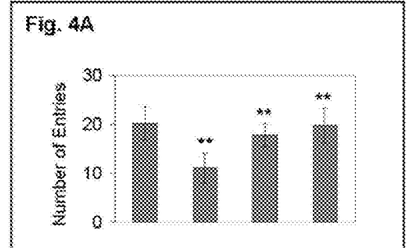
FIG. 4A is a graph showing that maternally blocking the STAT3 signal pathway with diosmin opposes IL-6-induced abnormal behavior in MIA/adult offspring as shown by the results of the open-field test. In the open-field test, offspring of mice treated with either S31-201 or diosmin enter the center more often than those treated only with IL-6 (**P<0.01) and are nearly similar to control mice. Offspring of mice intraperitoneally (i.p.) treated with IL-6 (5 g/mouse) in the absence or presence of STAT3 inhibitor S31-201 (4 g/mouse; i.p.) or with diosmin (10 mg/kg/day; oral administration).

The adult offspring of these mice were examined for behavioral outcomes using the open field and social interaction tests to examine anxiety and social interaction, respectively. Our results demonstrate that S31-201 or diosmin co-treatment significantly attenuates the behavioral deficits seen in the adult offspring of IL-6 treated animals. In the open-field test, offspring of mice treated with either S31-201 or diosmin showed behaviors comparable to that of control mice, entering the center more often than IL-6 treated animals (**$P<0.01$) (FIG. 4A). In addition, an ANOVA on time spent in the inner section showed a significant main effect of group ($P<0.05$) and LSD post hoc tests showed that the IL-6/MIA mice spend less time in the inner section compared to S31-201 or diosmin treated mice ($P<0.05$). As these could be due to simply increased locomotion in one group, ANOVA on distance traveled in the inner section was performed and did not indicate a main effect ($P=0.069$). Analyses of distance traveled in the outer section did not reveal a significant difference or a statistical trend towards a significant difference (P>0.15) among groups. We did not find a significance between PBS-treated mice and S31-treated control (non-IL-6 injected) mice (P>0.05 with n=5).

Figure 4B:
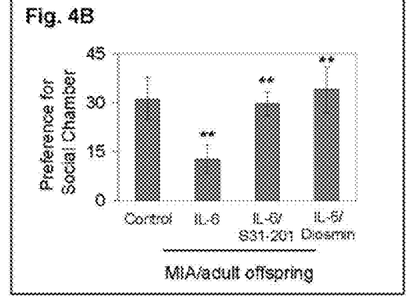
FIG. 4B is a graph showing that maternally blocking the STAT3 signal pathway with diosmin opposes IL-6-induced abnormal behavior in MIA/adult offspring as shown by the results of the social interaction test. In the social interaction test, the social chamber is defined as (the percentage of time in the social chamber)−(the percentage of time in the opposite chamber). Control mice reveal a strong preference for the social chamber. Offspring of mice treated with either S31-201 or diosmin also enter the social chamber more often than those treated only with IL-6 (**P<0.005) and are nearly similar to control mice. Offspring of mice intraperitoneally (i.p.) treated with IL-6 (5 g/mouse) in the absence or presence of STAT3 inhibitor S31-201 (4 g/mouse; i.p.) or with diosmin (10 mg/kg/day; oral administration).

As shown in FIG. 4, maternally blocking STAT3 signal pathway with diosmin opposes IL-6-induced abnormal behavior in MIA/adult offspring. Offspring of mice (n=8, 4 female/4 male) intraperitoneally (i.p.) treated with IL-6 (5 µg/mouse) in the absence or presence of STAT3 inhibitor (S31-201; 4 µg/mouse; i.p.) (Siddiquee et al. 2007) or with diosmin [oral administration; (10 mg/kg/day)]. FIG. 4A shows that in the open-field test, offspring of mice treated with either S31-201 or diosmin enter the center more often than IL-6 ($P<0.01$) and are nearly similar to control mice. Heightened anxiety and social interaction deficits are hallmarks of schizophrenia and autism. Reluctance to enter the center portion of a well-lit open field is usually taken as a measure of heightened anxiety under mildly stressful conditions (Smith et al., 2007). FIG. 4B shows that in the social interaction test, as previously reported, the social chamber was defined as (percentage of time in social chamber)-(percentage of time in opposite chamber). Most notably, control mice reveal a strong preference for the social chamber. Interestingly, the social impairment of offspring is significantly improved by maternal administration of STAT3 inhibitor, S31-201 or diosmin ($P<0.005$).

In the social interaction test, the adult offspring of control mice show a strong preference for the social chamber almost double that of the adult offspring of IL-6 treated mice. To quantify social interaction, exploration demonstrated as sniffing time was analyzed via ANOVA. There was a main effect of group ($P<0.05$); the S31-201 or diosmin mice exhibited an increase in sniffing compared to IL-6/MIA mice ($P<0.05$). We did not observe any social grooming, chasing, dominant mounts, pinning, boxing, or biting. There were no significant differences in total move time (P>0.07) and total distance traveled (P>0.05).

This social impairment observed in IL-6 adult offspring was significantly attenuated by maternal co-treatment with S31-201 or diosmin as these mice show a preference for the social chamber comparable to that of control adult offspring (**$P<0.005$) (FIG. 4B). Considering the above data, it can be seen that IL-6 induced JAK2/STAT3 phosphorylation plays an essential role in precipitating behavioral abnormalities seen in the adult offspring of IL-6 treated dams and regulation of this pathway by diosmin can attenuate these behavioral abnormalities.

Diosmin Reduces Pro-Inflammatory Cytokines and STAT3 Phosphorylation in IL-/MIA Adult Offspring After behavioral testing, adult offspring were sacrificed to confirm that inhibition of STAT3 phosphorylation by diosmin attenuates IL-6/JAK2/STAT3 induced behavioral abnormalities. At sacrifice, brain homogenates were prepared from offspring of control mice and mice treated with IL-6, IL-6/S31-201, and IL-6/Diosmin. Pro-inflammatory cytokine ELISA showed significant increase in TNF-α and IL-1β levels in the homogenates of IL-6 adult offspring. Maternal co-treatment with S31-201 or diosmin significantly reduces TNF-α and IL-1β cytokine levels significantly, with diosmin showing slightly more significant reductions as shown in FIG. 5 (**$P<0.05$).

Figure 5:
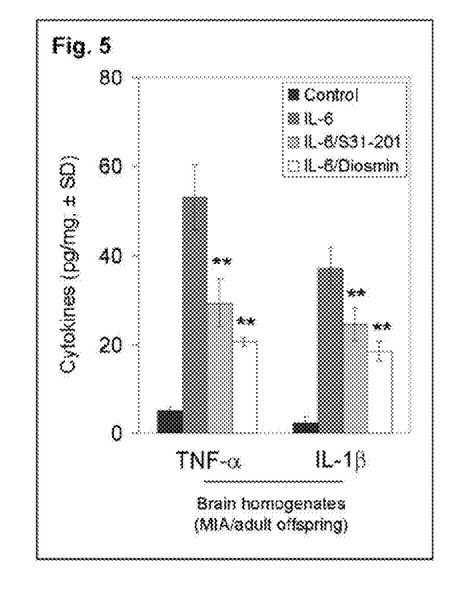
FIG. 5 is a graph showing that diosmin reduces pro-inflammatory cytokines Brain homogenates were prepared from offspring of mice treated with IL-6, IL-6/S31-201, IL-6/diosmin or PBS (control). Pro-inflammatory cytokine analysis by ELISA was conducted on the mouse brain homogenates. Data are represented as mean±SD of each cytokine in brain homogenates (pg/mg total protein) from these mice. Analysis of results revealed a significant reduction of TNF- and IL1 cytokines in brain homogenates from IL-6/S31-201 and IL-6/diosmin adult offspring when compared to MIA only mothers (IL-6 treatment only) (**P<0.05).

As shown in FIG. 5, Diosmin reduces pro-inflammatory cytokines in IL-6/MIA adult offspring. At sacrifice, brain homogenates were prepared from offspring of mice treated with IL-6, IL-6/S31-201, IL-6/Diosmin or PBS (control) (n=8, 4 female/4 male). Pro-inflammatory cytokine analysis by ELISA was conducted on these mouse brain homogenates. Data are represented as mean±SD of each cytokine in brain homogenates (pg/mg total protein) from these mice. Analysis of results revealed a significant reduction of TNF-α and IL-1β cytokines in brain homogenates from IL-6/31-201 and IL-6/Diosmin adult offspring when compared to offspring of MIA only mothers (IL-6 treatment only) (**$P<0.05$).

Western blot analysis of phospho- and total STAT3 shows that IL-6 treatment of dams increases STAT3 phosphorylation in the brain homogenates of adult offspring while co-treatment with either S31-201 or diosmin leads to a significant reduction of STAT3 phosphorylation (**$P<0.005$) (FIG. 6).

Figure 6A:
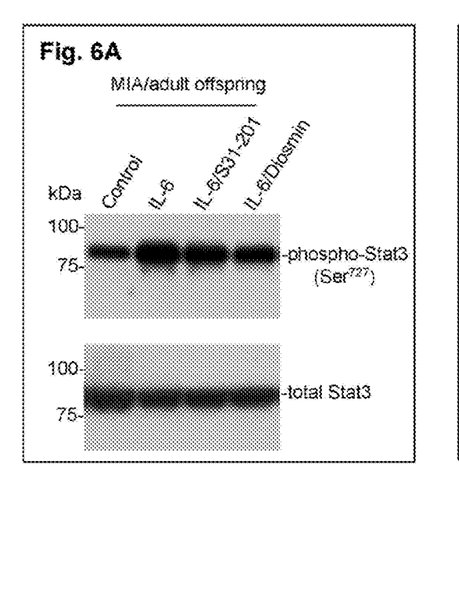
FIG. 6A is an image of a Western Blot Analysis showing a notable reduction in STAT3 phosphorylation in brain homogenates from IL-6/S31-201 and IL-6/diosmin adult offspring when compared to the offspring of MIA-only mothers (IL-6 treatment only). Western Blot Analysis was conducted with antibodies specifically against phosphor-STAT3 (Ser$^{727}$) and total STAT3.
Figure 6B:
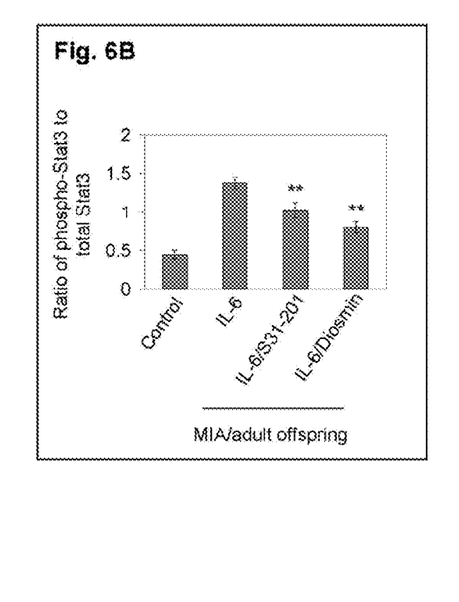
FIG. 6B is a graph showing the results of densitometry analysis revealing the ratio of phosphor-STAT3 to total STAT3. Analysis of results showed a significant reduction of STAT3 phosphorylation from IL-6/S31-201 and IL-6/diosmin adult offspring when compared to offspring of MIA-only (IL-6 treatment only) mothers (**P<0.005).

As shown in FIG. 6, Diosmin reduces STAT3 phosphorylation in IL-6/MIA adult offspring. FIG. 6A shows a Western blot analysis with antibodies specifically against phospho-STAT3 (Ser$^{727}$) and total STAT3 shows a notable reduction of STAT3 phosphorylation in brain homogenates from IL-6/S31-201 and IL-6/Diosmin/adult offspring when compared to offspring of MIA only mothers (IL-6 treatment only). The densitometric analysis shown in FIG. 6B reveals the ratio of phospho-STAT3 to total STAT3 as indicated below the figure. In support, analysis of results showed a significant reduction of STAT3 phosphorylation from IL-6/S31-201 and IL-6/Diosmin/adult offspring when compared to offspring of MIA only mothers (IL-6 treatment only) (**$P<0.005$).

Elucidating the mechanisms and pathways involved in neurodevelopmental disorders such as autism and schizophrenia is important in not only understanding the etiology of these disorders but also to discover early diagnostic markers, and prophylactic therapies, in addition to therapeutic strategies to attenuate the associated symptoms. Previous research by Smith and colleagues has supported the role of exogenous IL-6 in precipitating the behavioral deficits and increases in pro-inflammatory cytokine release seen in MIA offspring, and potentially autistic and schizophrenic individuals, in addition to demonstrating that its inhibition can attenuate these pathologies (Smith et al. 2007). We further examined the role of IL-6 in MIA by characterizing the role of JAK2/STAT3 phosphorylation in precipitating behavioral and pathological outcomes. We also determined if inhibition of this phosphorylation had the ability to attenuate these behavioral deficits and/or pathologies observed in the adult offspring of IL-6/MIA mice. Previous research by our laboratory has shown that bioflavonoids regulate STAT1 phosphorylation, as we showed that luteolin (Rezai-Zadeh et al. 2008) or EGCG (Giunta et al. 2006) inhibited IFN-γ induced STAT1 phosphorylation. We examined if diosmin, a luteolin analog with better bioavailability, had similar effects, inhibiting IL-6 induced STAT3 phosphorylation.

We confirmed the role of IL-6 induced JAK2/STAT3 phosphorylation in precipitating pathological and behavioral deficits seen previously in IL-6/MIA animal models. The results of our study demonstrate that IL-6 induces JAK2/STAT3 phosphorylation resulting in the release of pro-inflammatory cytokines both in vitro and in vivo. Western blot analyses of cell lysates from murine N2a cells and primary cultured neuronal cells showed time-dependent increases in JAK2/STAT3 phosphorylation following IL-6 treatment. Analysis of brain homogenates of newborn mice from IL-6 treated dams similarly showed increases in JAK2/STAT3 phosphorylation, in addition to increases in released pro-inflammatory cytokines TNF-α and IL-1β.

We measured IL-6 levels in brain homogenates from the offspring using ELISA. The level of IL-6 was undetectable which is in contrast to the results previously reported by Samuelsson et al. 2006. As previously mentioned, this group found that IL-6 mRNA levels remain elevated in the hippocampi of the offspring at 4 and 24 weeks of age; indicative of the ongoing state of immune dysregulation in adult autistic brains. We thus suggest IL-6 itself may not be a contributory factor for the in vivo chronic inflammatory pathogenic affects, but rather for the in utero effects. Therefore measuring IL-6 in the offspring may not be representative of its exposure in utero. Rather, the indirect effects of IL-6 pro-inflammatory activation in utero of the JAK2/STAT3 pathway, as evidenced by increased TNF-α and IL-1β production, may be at play in an autism mouse phenotype. Thus, with evidence that JAK2/STAT3 phosphorylation induced pathological outcomes in the offspring of IL-6 treated animals, we examined whether or not this phosphorylation contributed to the behavioral deficits observed in the offspring of IL-6 treated dams.

There is much epidemiologic evidence indicating that environmental contributions, including prenatal infections which can lead to MIA, may lead to the genesis of autism (Arndt et al. 2005 and Libbey et al 2005). Previous animal models, developed by Fatemi and Folsom 2009 and others, have shown that immune challenges during pregnancy lead to abnormal brain structure and function in the exposed offspring that replicate abnormalities observed in brains of subjects with autism (Fatemi et al. 2005, Fatemi et al. 2008, Meyer et al. 2006, Meyer et al. 2007 and Shi et al. 2005). Abnormal CNS changes in the offspring following infection at E9, which corresponds to infection at the middle of the first trimester (Fatemi et al. 2005 and Shi et al. 2003), and E18, which corresponds to infection in late second trimester (Fatemi et al. 2008) have been previously shown. Importantly E16 immediately follows the period of neurogenesis of hippocampal pyramidal cells (E11-E15.5) (Rodier 1980). Thus we hypothesized that middle second trimester infection (E12.5, E15 and E17) in mice would alter brain cytokine expression of the offspring since Fatemi and Folsom 2009 found that infection at E16 leads to altered expression of many brain genes in the hippocampi of the exposed mouse offspring.

Our results showed that the adult offspring of IL-6 treated animals displayed behavioral deficits in social interaction and regulation of anxiety that are reminiscent of autism. We also found neuropathology previously described (Turner 1999) including increase pro-inflammatory cytokine release and increased STAT3 phosphorylation. In many previous works by other groups the pre-pulse inhibition (PPI) test is particularly informative for animal models of autism, because there are existing models for understanding the neural circuitry of startle gating; a process known to involve inhibitory corticostriatal neural circuits (Braff et al. 2001). Furthermore, sensorimotor gating deficits have been reported in a family of neurodevelopmental disorders and are not specific to autism. Whereas Ornitz et al. 1993 reported equivocal PPI results in autistic children, others reported PPI deficits in adults with Asperger syndrome (McAlonan et al. 2002), children with Tourette syndrome (Swerdlow et al 2001), and men with fragile X syndrome (Frankland et al. 2004). To date, only one published study on adults with autism (14 adult men diagnosed with autism and 16 typically developing normal comparison (NC) participants) has been conducted on the subject and it concluded that PPI deficits may only be indirectly linked to one of the hallmark features of autism. With this in mind we did not measure PPI in this study because if it were normal, it would have no scientific impact on the validity of the model, and it if were abnormal, it in itself would not be a measure of true neuropsychiatric impairment, rather the functional behavioral tests we performed would.

As a confirmation of our results, we examined the effects of luteolin and diosmin in regulating IL-6 induced JAK2/STAT3 phosphorylation in vitro and if this could attenuate the pathologies and behavioral deficits previously described. When murine N2a cells and primary cultured neuronal cells were co-treated with IL-6 and luteolin, we observe a concentration dependent decrease in JAK2/STAT3 phosphorylation, as evidenced by Western blot analysis of cell lysates. We next examined the in vivo effects of diosmin, with the STAT3 inhibitor S31-201 as a positive control. When pregnant mice were co-treated with IL-6 and either diosmin, or S31-201, we observed an attenuation of the behavioral deficits in the adult offspring of diosmin and S31-201 co-treated animals as they showed social behaviors comparable to that of control mice. Furthermore, when brain homogenates of these adult offspring were examined, we saw decreased STAT3 phosphorylation with decreased pro-inflammatory cytokine secretion.

Taken together, our results show that IL-6 induced JAK2/STAT3 phosphorylation plays an integral role in the execution of IL-6/MIA mediated pathological effects. Indeed, inhibition of this phosphorylation was able to attenuate both behavioral deficits and pathological outcomes such as increased inflammation.

Treatment with diosmin is not only effective, but safe. Indeed diosmin is a natural flavonoid isolated from various plant sources or derived from the flavonoid hesperidin. First used as a therapy in 1969, diosmin is currently considered a vascular-protecting agent and has been used for treatment of chronic venous insufficiency/varicose veins (Jantet 2002), hemorrhoids (Jantet 2000), lymphedema (Pecking et al. 1997), and diabetes (Lacombe et al. 1989). The compound also exhibits anti-inflammatory, antioxidant, and antimutagenic properties (Kuntz et al. 1999). Furthermore, marketed formulations 90% diosmin, 10% hesperiden pose little to no side effects. Taken together, there is convincing evidence from preliminary studies regarding efficacy, as well as published studies regarding safety in humans, that diosmin is a safe and potentially efficacious treatment for autism. Furthermore, the dose found to be effective in this animal model (10 mg/kg/day) translates into a human dose of 0.81 mg/kg/day which is approximately 48.6 mg/day for a 60 kg person. While not reasonably achievable through consumption of foods containing diosmin, this concentration may be provided through a daily oral supplement.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of reducing the risk of developing autism in a patient due to exposure of the patient in utero to elevated levels of IL-6 from the patient's mother-comprising:
   inhibiting activation of STAT3 in both the patient and the patient's mother by administering a therapeutically effective amount of a flavonoid selected from the group consisting of luteolin, diosmin, and diosmetin to the patient's mother during pregnancy;

wherein STAT3 in the patient and the patient's mother is activated by elevated levels of IL-6 from the patient's mother.

2. The method of claim 1, wherein the flavonoid is administered orally.

3. The method of claim 1, wherein the flavonoid is administered at a dosage of between about 0.81 mg/kg/day and about 2.5 mg/kg/day.

4. The method of claim 1, wherein the patient's mother suffered from an infection which resulted in maternal immune activation of IL-6 while pregnant.

5. The method of claim 3, wherein the flavonoid is diosmin.

6. A method of treating autism in a patient in utero comprising:
   obtaining levels of IL-6 in a mother of the patient;
   comparing the levels of IL-6 from the mother to a control level wherein an elevated level of IL-6 from the mother as compared to the control level is indicative of STAT3 activation; and
   inhibiting the activation of STAT3 by administering a therapeutically effective amount of a flavonoid selected from the group consisting of luteolin, diosmin, and diosmetin to the mother;
   wherein inhibiting STAT3 activation in the mother also inhibits STAT3 activation in the patient.

7. The method of claim 6, wherein the flavonoid is administered orally.

8. The method of claim 6, wherein the flavonoid is administered at a dosage of between about 0.81 mg/kg/day and about 2.5 mg/kg/day.

9. The method of claim 6, wherein TNF-α and IL-1β levels are increased in the patient as compared to a control level.

10. The method of claim 9, wherein the flavonoid is diosmin.

11. A method of reducing the risk of developing schizophrenia in a patient due to exposure of the patient in utero to elevated levels of IL-6 from the patient's mother comprising:
    inhibiting activation of STAT3 in both the patient and the patient's mother by administering a therapeutically effective amount of a flavonoid selected from the group consisting of luteolin, diosmin, and diosmetin to the patient's mother during pregnancy;
    wherein STAT3 in the patient and the patient's mother is activated by elevated levels of IL-6 from the patient's mother.

12. The method of claim 11, wherein the flavonoid is administered orally.

13. The method of claim 11, wherein the flavonoid is administered at a dosage of between about 0.81 mg/kg/day and about 2.5 mg/kg/day.

14. The method of claim 11, wherein the mother suffered from an infection which resulted in maternal immune activation of IL-6 while pregnant.

15. The method of claim 13, wherein the flavonoid is diosmin.

* * * * *